United States Patent
Zhang

(10) Patent No.: US 12,121,207 B2
(45) Date of Patent: Oct. 22, 2024

(54) ENDOSCOPE

(71) Applicant: SCIVITA MEDICAL TECHNOLOGY CO., LTD., Suzhou (CN)

(72) Inventor: Yi Zhang, Suzhou (CN)

(73) Assignee: SCIVITA MEDICAL TECHNOLOGY CO., LTD., Suzhou (CN)

( * ) Notice: Subject to any disclaimer, the term of this patent is extended or adjusted under 35 U.S.C. 154(b) by 401 days.

(21) Appl. No.: 17/597,301

(22) PCT Filed: Nov. 13, 2019

(86) PCT No.: PCT/CN2019/117812
§ 371 (c)(1),
(2) Date: Dec. 30, 2021

(87) PCT Pub. No.: WO2021/000490
PCT Pub. Date: Jan. 7, 2021

(65) Prior Publication Data
US 2022/0313064 A1    Oct. 6, 2022

(30) Foreign Application Priority Data

Jul. 4, 2019 (CN) .......................... 201910600626.9

(51) Int. Cl.
*A61B 1/00* (2006.01)
*A61B 1/05* (2006.01)

(52) U.S. Cl.
CPC ...... *A61B 1/00066* (2013.01); *A61B 1/00071* (2013.01); *A61B 1/00186* (2013.01); *A61B 1/05* (2013.01)

(58) Field of Classification Search
CPC ............ A61B 1/00066; A61B 1/00071; A61B 1/00186; A61B 1/05; A61B 1/227
(Continued)

(56) References Cited

U.S. PATENT DOCUMENTS 3,456,641 A * 7/1969 Yutaka ............... G02B 23/2469
607/93
4,310,071 A * 1/1982 Plow ....................... F16N 21/06
184/88.1
(Continued)

FOREIGN PATENT DOCUMENTS

CN    107105978 A    8/2017
CN    109222880 A    1/2019
(Continued)

OTHER PUBLICATIONS

ISR of PCT/CN2019/117812.

*Primary Examiner* — Timothy J Neal
*Assistant Examiner* — James Edward Boice
(74) *Attorney, Agent, or Firm* — Bayramoglu Law Offices LLC

(57) ABSTRACT

An endoscope comprising a camera handle used to fix the camera lens and a wired connector; the camera handle comprises of an outer shell, an end cap and an inner shell; an sensing element is provided inside the inner shell; a lens group is provided between the sensing element and the end cap; the inner shell is fixedly connected with the outer shell through assembling components; the outer shell is fixedly connected with the inner shell through fixing components; a light hole corresponding to the position of the sensing element is cut in the middle of the end cap. The present invention has following advantages: The inner shell is inside the outer shell; both the inner shell and the outer shell are fixedly connected with the end cap; overall sealing, waterproof and dustproof performances of the camera handle are excellent; the removable waterproof cover is provided at the end of the sleeve; the elastic sealing ring is provided between the waterproof cover and the assembling tube; the connector is in a sealed space and protected from being damaged by penetrated disinfectant; with excellent water- (Continued)

proof performance and safe use, the wired connector is suitable for medical equipment.

8 Claims, 16 Drawing Sheets

(58) Field of Classification Search
USPC .................................................. 600/104, 200
See application file for complete search history.

(56) References Cited

U.S. PATENT DOCUMENTS

| | | | | |
|---|---|---|---|---|
| 4,869,719 | A * | 9/1989 | Hogan | A61M 25/02 |
| | | | | 604/174 |
| 5,097,529 | A * | 3/1992 | Cobb | G02B 6/4442 |
| | | | | 385/135 |
| 6,201,880 | B1 * | 3/2001 | Elbaum | A61B 1/24 |
| | | | | 348/66 |
| 6,554,765 | B1 * | 4/2003 | Yarush | A61B 1/00108 |
| | | | | 600/109 |
| 9,814,380 | B1 | 11/2017 | Silva et al. | |
| 2014/0012075 | A1 * | 1/2014 | Konstorum | A61B 1/0052 |
| | | | | 600/104 |
| 2015/0073212 | A1 * | 3/2015 | Yamazaki | A61B 1/0615 |
| | | | | 600/179 |
| 2017/0064430 | A1 * | 3/2017 | Zheng | H05K 5/0017 |

FOREIGN PATENT DOCUMENTS

| | | | |
|---|---|---|---|
| CN | 208970823 | A | 6/2019 |
| CN | 110251057 | A | 9/2019 |
| JP | 2006136671 | A | 6/2006 |

* cited by examiner

A

B

C

ENDOSCOPE

FIELD OF THE INVENTION

The present invention involves a medical device, more particularly, an endoscope.

STATE OF THE ART

Endoscope is a medical device used to observe pathological changes in a patient's organ or tissues; it is usually used together with a monitor, an image processor and a cold light source to observe tissues or finish a surgery. When observing pathological tissues, the doctor inserts the working end of the endoscope inside the patient; the cold light source enters the patient through the optical fiber in the endoscope and provides lighting for the micro camera inside the patient; the micro camera shoots images of the patient's organ; the doctor analyzes and judges the patient's conditions on basis of the organ images which are shot from different angles, processed and displayed on the monitor.

Before above operation, all surgical devices need to be disinfected, including the camera and the wired connector. As for the camera, the camera of the endoscope may contact blood or body fluids during a surgery; if any device of the endoscope is of insufficient sealing, liquid may penetrate into such device through gaps, and the imaging quality may not be stable during the surgery. As for the wired connector, the wiring port of the connector is exposed, disinfection by soaking or wiping with disinfectant may leave liquid on the connector, and the service life and safety of the connector will be affected. Therefore, relevant structures of the endoscope shall be well sealed, and such structures shall guarantee the imaging quality of the camera.

SUMMARY OF THE INVENTION

The present invention provides an endoscope, aiming at solving above issues.

In order to achieve above objectives, the present invention provides an endoscope comprising a camera handle used to fix the camera lens, and a wired connector which is connected to power supply and provides power for the camera lens; the camera handle comprises of an outer shell, an end cap inserted and assembled at the end of the outer shell, an inner shell inside the outer shell and an sensing element inside the inner shell; a lens group is set between the sensing element and the end cap; the inner shell is fixedly connected with the outer shell through assembling components; the outer shell is fixedly connected with the inner shell through fixing components; a light hole corresponding to the position of the sensing element is cut in the middle of the end cap.

In an embodiment of the end cap of the camera handle, an insertion section is provided at the edge of the end cap to be inserted into and connected with the outer shell; a fixing groove is arranged on the outer ring surface of the insertion section; a sealing ring I is provided in the fixing groove; the fixing components comprise multiple anchor bolts inserted into the end cap; multiple insertion tubes corresponding to the anchor bolts are set on the inner side wall of the outer shell; each of the anchor bolts comprises a bolt head and a bolt shank, each bolt shank comprises a sealing section connected with the bolt head and an insertion section with a diameter smaller than that of the sealing section; ring grooves are arranged on the sealing sections of the bolt shanks, and sealing rings II are provided in the ring grooves; sleeves are sleeved onto the insertion sections of the bolt shanks; the sleeves transiently fit with the insertion sections of the anchor bolts and the insertion tubes.

The structure of the lens group and the sensing element: A washer is provided between the lens group and the sensing element; a fixing groove is arranged at the position of the light hole on the end cap for assembling the lens group; the lens group comprises a dust blocking lens and a light filtering lens; the light filtering lens is provided between the dust blocking lens and the washer; a clamping frame is provided at the edge of the light filtering lens; the clamping frame is of C-shape and has a clamping open on the side toward the dust blocking lens for clamping the light filtering lens; the clamping frame is fixedly connected with the end cap.

The lens group is fixed and assembled at the light hole on the end cap by following steps:

S1. Apply a layer of UV sealant on the bottom wall of the fixing groove, assemble the dust blocking lens in the fixing groove, and cure UV sealant with a UV light source;

S2. Fill UV sealant into the gaps between the dust blocking lens and the side walls of the fixing groove, and cure UV sealant with a UV light source;

S3. Clamp the light filtering lens into the clamping open of the clamping frame, assemble the light filtering lens and the clamping frame in the fixing groove, make the light filtering lens tightly press the dust blocking lens, and fix the clamping frame;

S4. Fill UV sealant into the gaps between the clamping frame, the light filtering lens and the side walls of the fixing groove, cure UV sealant with a UV light source; the lens group is assembled.

In an embodiment of the wired connector, the wired connector comprises of a wire, a connector connected with the wire and a sleeve wrapping the connector; the end of the connector extends beyond the sleeve; a waterproof cover is provided around such extension section; the waterproof cover is cylindrical, one of its end is open, and the other end is closed; a waterproof sealing assembly is provided at the end of the sleeve away from the waterproof cover for fixing the wire.

The sleeve comprises a coaxially arranged assembling tube, and a fixing tube with an outer diameter smaller than that of the assembling tube; a spacer plate is provided at the connection of the assembling tube and the fixing tube; the connector is inserted into the assembling tube; an assembling ring groove is arranged on the inner circumferential side wall of the waterproof cover; an elastic sealing ring is provided in the assembling ring groove for fitting with the outer circumferential side wall of the sleeve.

In an embodiment of the waterproof sealing assembly, the waterproof sealing assembly comprises a sealing tube, a fixing ring and a removable locking sleeve connected with the fixing tube; the sealing tube is set around the wire; an insertion tube is provided at the end of the sealing tube and inserted into the fixing tube; a limit ring edge I is arranged on the outer circumferential side wall at the end of the insertion tube fitting with a spacer plate; the fixing ring is set around the insertion tube; one end of the fixing ring is inserted into the fixing tube; a limit ring edge II is arranged on the outer circumferential side wall at the other end of the fixing ring for fitting with the end surface of the fixing tube; a limit ring edge III with an inner diameter smaller than the outer diameter of the limit ring edge II is arranged on the inner circumferential side wall at the end of the locking sleeve away from the spacer plate; several positioning parts are provided on the wall of the sleeve for fixing the connector; a connecting part is provided between the sleeve and the waterproof cover; the connecting part comprises a lantern ring I set around the waterproof cover, a lantern ring II set around the sleeve, and a flexible rope connecting the lantern ring I and the lantern ring II.

The present invention has following advantages: 1. The inner shell is inside the outer shell; both the inner shell and the outer shell are fixedly connected with the end cap; overall sealing, waterproof and dustproof performances of the camera handle are excellent; under a double protection provided by the inner shell and the outer shell, the built-in sensing element is not easily affected by external interference factors, so the excellent stability of the camera handle is ensured during operation. A sensor is fixed with a fixing block, a positioning block and a fixing bolt, the number of the threads arranged on the shell of the camera handle is minimized, overall sealing performance of the camera handle is improved, and the sensor does not directly contact with the inner shell; under a double protection provided by the inner shell and the outer shell, the sensor is not easily affected by external interference factors, disinfectant and body fluids can't easily penetrate and damage the imaging elements inside the camera handle; dust and moisture are effectively blocked by the dust blocking lens of the lens group, interference light waves are filtered by the light filtering lens of the lens group, and the imaging quality is improved. The high-stability camera handle of the endoscope under the present invention has the advantages of stable imaging and excellent anti-interference, dust-proof and waterproof performances.

2. The removable waterproof cover is provided at the end of the sleeve; an elastic sealing ring is set between the waterproof cover and the assembling tube; the connector is in a sealed space and protected from being damaged by penetrated disinfectant; with excellent waterproof performance and safe use, the wired connector is suitable for medical equipment. The connector protected in a relatively sealed space, which is formed by the removable sleeve provided at the assembling tube of the sleeve and the waterproof sealing assembly provided at the fixing tube of the sleeve, is suitable for medical equipment. Before disinfection, the waterproof cover is sleeved onto the end of the sleeve to effectively prevent disinfectant from penetrating and damaging the connector, the waterproof performance is excellent. When the wired connector is not being used, the connector is in a relatively sealed space and will not be polluted by dust or bacteria, it is clean and sanitary. Moreover, the connector is protected by the waterproof cover from being damaged in case of dropping the wired connector.

BRIEF DESCRIPTION OF THE DRAWINGS

In FIGS. 1-16: 1. Outer shell; 11. Insertion tube; 12. Clamping open; 2. End cap; 21. Insertion section; 211. Fixing groove; 2111. Sealing ring I; 22. Stepped hole; 23. Anchor bolt; 231. Sleeve; 232. Ring groove; 233. Sealing ring II; 24. Sinking groove; 241. Light hole; 242. Assembling groove; 243. Clamping groove I; 2431. Clamping groove; 244. Clamping groove II; 25. Spacer block; 26. Washer; 261. Through-hole; 3. Inner shell; 31. Fixing plate; 311. Fixing lug; 32. Radiating plate; 3. Assembling plate; 4. 3MOS sensor; 41. Fixing block; 42. Positioning block; 421. Positioning lug; 43. Fixing bolt; 44. Positioning hole; 5. Lens group; 51. Dust blocking lens; 52. Light filtering lens; 53. Clamping frame; 531. Clamping open; 6. Fixing block I; 61. Fixing plate I; 62. Clamping block; 7. Fixing block II; 71. Fixing plate II; 10. Sleeve; 101. Assembling tube; 1011. Clamping ring edge I; 102. Fixing tube; 1021. Clamping ring edge II; 103. Positioning part; 104. Spacer plate; 20. Waterproof cover; 201. Ring groove I; 202. Assembling ring groove; 2021. Elastic sealing ring; 30. Wire; 40. Connector; 50. Sealing tube; 501. Insertion tube; 5011. Limit ring edge I; 60. Fixing ring; 601. Limit ring edge II; 70. Locking sleeve; 701. Limit ring edge III; 702; Ring groove II; 80. Connecting part; 801. Lantern ring I; 802. Lantern ring II; 803. Flexible rope; 90. Groove.

DETAILED DESCRIPTION OF THE EMBODIMENTS

Figure 1:
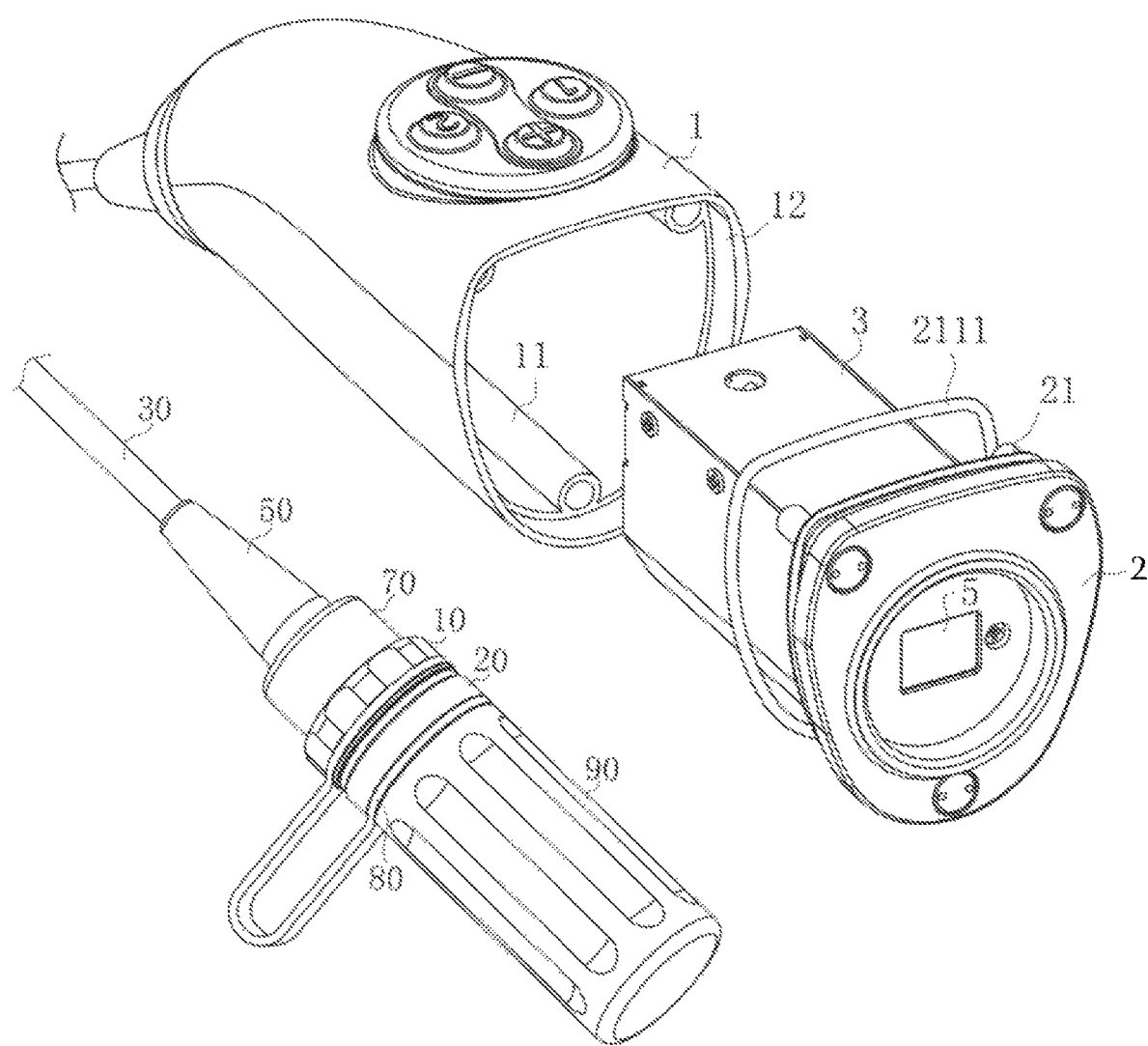
FIG. 1 is an overall structural view of the camera handle and the wired connector.
Figure 2:
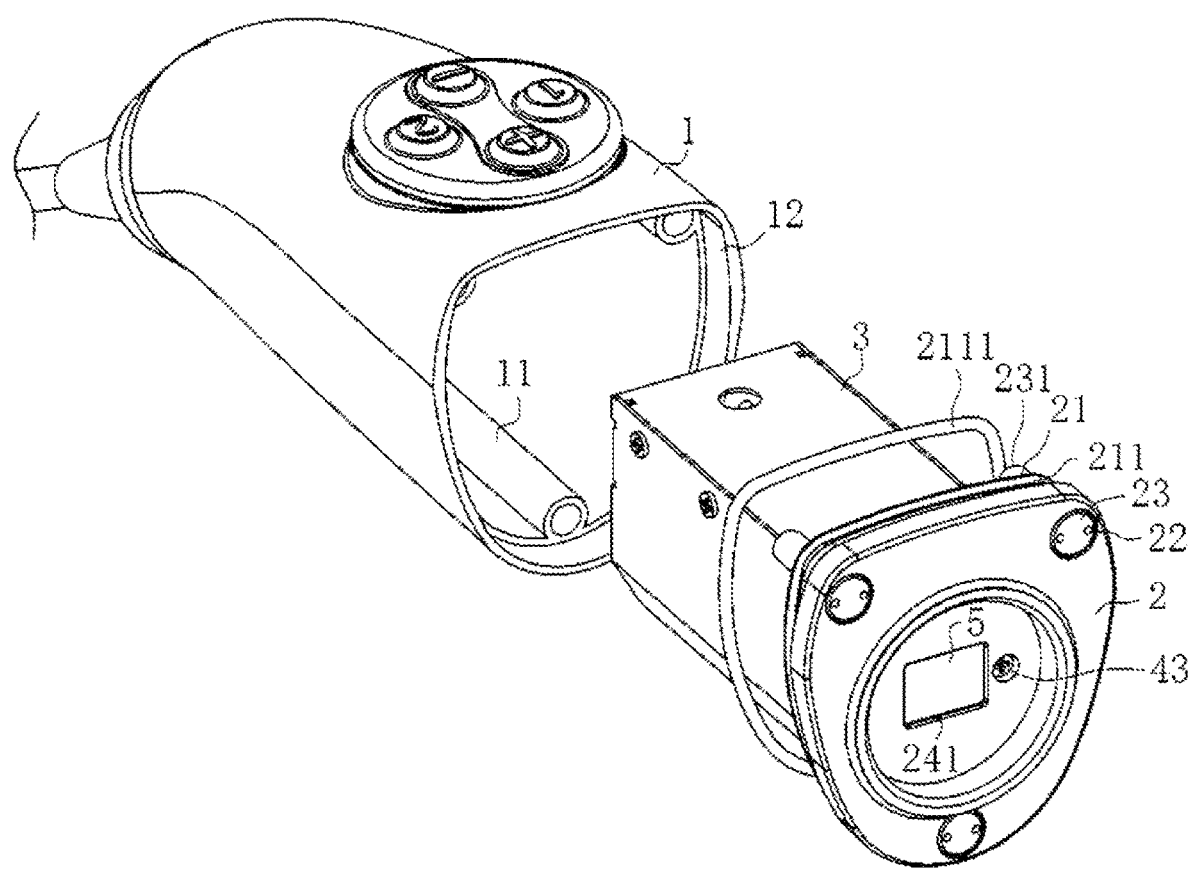
FIG. 2 is an exploded view of the camera handle in the embodiment.

In order to enable those skilled in the art to better understand the technical scheme of the invention, the present invention is clearly and fully described below in conjunction with the accompanying drawings. As shown in FIGS. 1-2, the camera handle comprises an outer shell 1, an inner shell 3 and an end cap 2. A signal wire used to transmit signals is connected with one end of the outer shell 1; the other end of the outer shell 1 is an open end for fixing the end cap. Three insertion tubes 11 are provided on the inner side wall of the outer shell 1 and along the length of the outer shell 1; a clamping groove 12 is arranged on the inner side wall at the open end of the outer shell 1. A light hole 241 is cut in the center of the end cap 2; a lens group 5 is provided at the light hole 241. The inner shell 3 is inside the outer shell 1 and of a rectangular box shape, one of its end toward the end cap 2 is an open end for fixing and connecting with the end cap 2. An insertion section 21 is provided at the end of the end cap 2 toward the outer shell 1; when assembling the end cap 2, with the clamping and fitting between the insertion section 21 and the clamping groove 12 on the outer shell 1, the end cap 2 is preliminarily fixed at the end of the outer shell 1.

Figure 4:
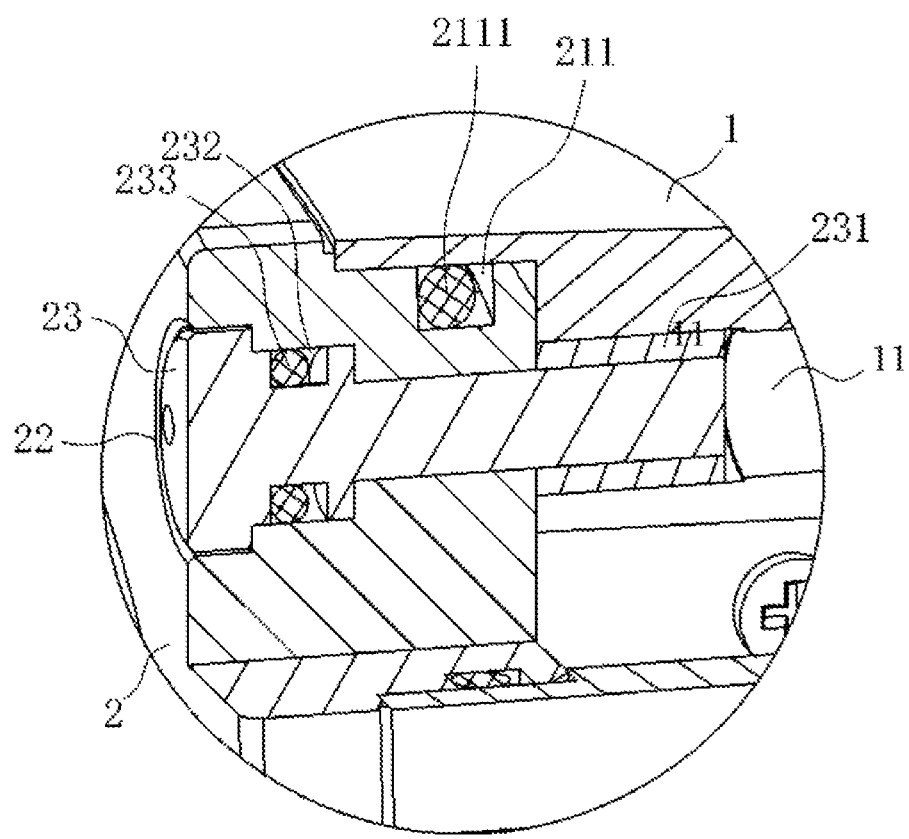
FIG. 4 is an enlarged view of Part A as shown in FIG. 3.

As shown in FIGS. 2 and 4, in order to enhance the tight fitting between the insertion section 21 and the clamping groove 12, a fixing groove 211 is arranged on the outer ring surface of the insertion section 21; a sealing ring I 2111 made of elastic rubber is provided in the fixing groove 211; after the insertion section 21 is inserted into the clamping grove 12, the sealing ring I 2111 tightly fits with the side walls of the clamping groove 12; assembling firmness, sealing and waterproof performances are improved.

Figure 3:
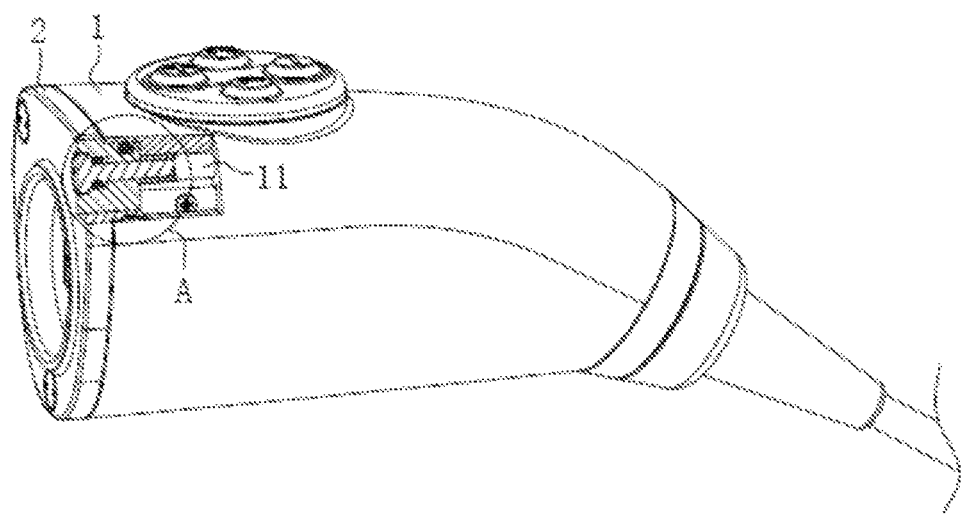
FIG. 3 is the sectional view I of the camera handle in the embodiment.

As shown in FIGS. 3-4, three stepped holes 22 are cut on the end cap 2; the anchor bolts 23 used to tighten the end cap 2 and the outer shell 1 are respectively inserted into the stepped holes 22. Each anchor bolt 23 comprises a bolt head and a bolt shank; the bolt shank is divided into two sections, the section connected with the bolt head has a diameter bigger than that of the section passing through and extending out of a stepped hole 22. Sleeves 231 are sleeved onto the bolt shanks of the anchor bolts 23; the sleeves 231 are provided at the side toward the inner cavity of the outer shell 1. The outer diameters of the sleeves 231 and the inner diameters of the insertion tubes 11 are the same. When fixing and locking the end cap 2, the anchor bolts 23 are inserted into the stepped holes 22 from the front of the end cap 2, the sleeves 231 are sleeved onto the ends of the anchor bolts 23 extending out the back of the end cap 2; in this way, the anchor bolts 23 will not fall from the end cap 2; after that, the end cap 2 is buckled onto the open end of the outer shell 1, meanwhile, the anchor bolts 23 and the sleeves 231 are inserted into the insertion tubes 11 to fix the end cap 2.

As shown in FIG. 4, the contact areas between the anchor bolts 23 and the stepped holes 22 are big, so the anchor bolts 23 will not get loose easily. In addition, ring grooves 232 are arranged on the sections with bigger diameter of the bolt shanks of the anchor bolts 23, and several sealing rings II 233 made of elastic rubber are provided in the ring grooves 232. The tight fitting between the anchor bolts 23 and the stepped holes 22 and sealing performance are further improved by providing the sealing rings II 233, excellent dustproof and waterproof performances of the camera handle are realized.

Figure 5:
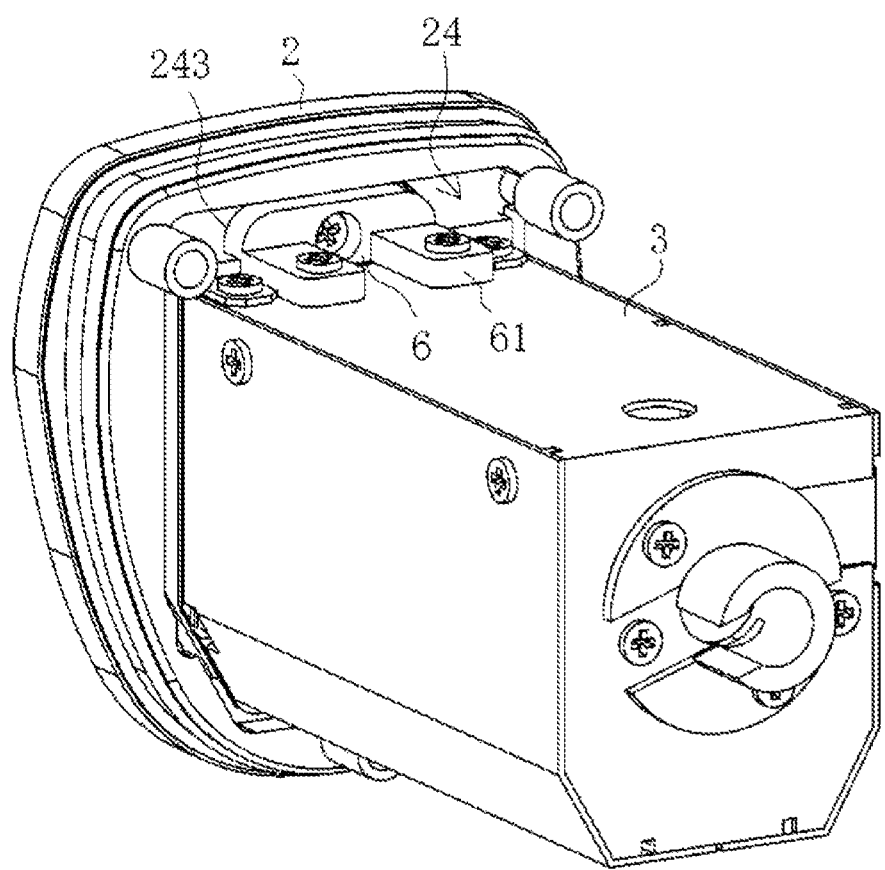
FIG. 5 is a structural view of the end cap and the inner shell in the embodiment.
Figure 6:
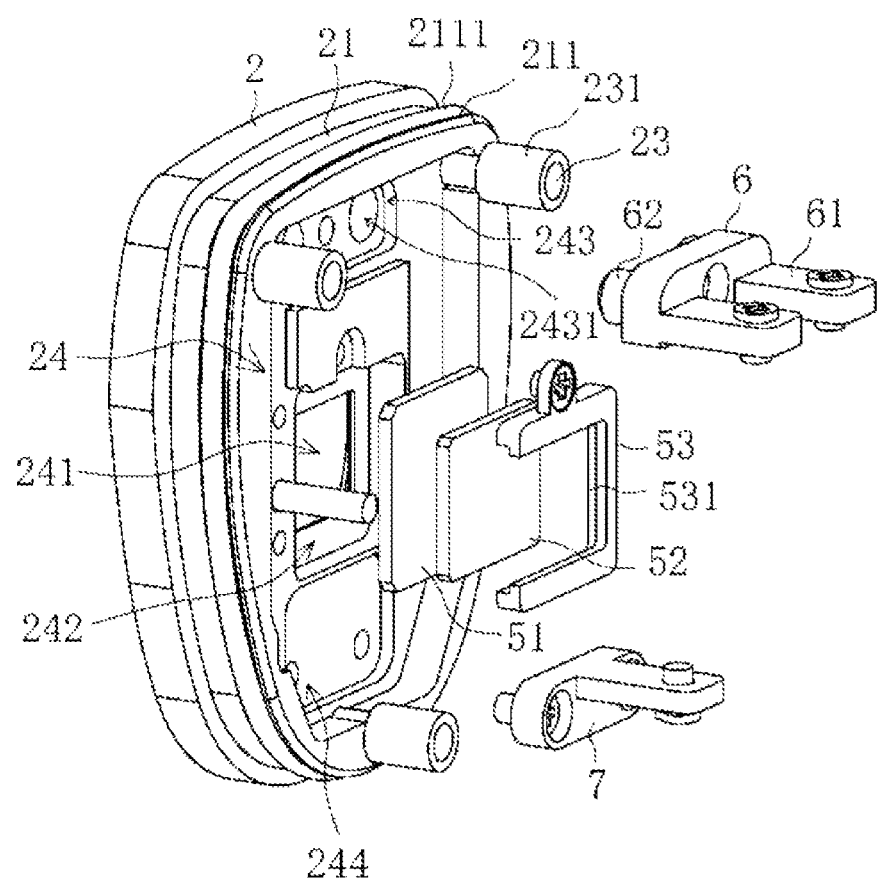
FIG. 6 is an exploded view of the end cap and the lens group in the embodiment.

As shown in FIGS. 5-6, a sinking groove 24 is arranged on the back of the end cap 2 for assembling different parts and fixing the inner shell 3; the end cap 2 and the inner shell 3 are connected and fixed through fixing components. Fixing components include a kidney-shaped strip fixing block I 6; a clamping groove I 243 is arranged in the sinking groove 24 for clamping the fixing block I 6. Two clamping blocks 62 are set at the end of the fixing block I 6 toward the end cap 2; two clamping grooves 2431 are arranged in the clamping groove I 243 for clamping the clamping blocks 62. Two fixing plates I 61 are set on the side of the fixing block I 6 away from the end cap 2; the fixing plates I 61 extend and fit with the outer top wall of the inner shell 3. During assembling, the fixing block I 6 is clamped into the clamping groove I 243, and the clamping blocks 62 are clamped into the corresponding clamping grooves 2431; after that, the fixing block I 6 is fixed in the clamping groove I 243 with a bolt; with the clamping and fitting between the fixing block I 6, the clamping blocks 62 and the clamping grooves 2431, the fixing block I 6 will not get loose easily; finally, the fixing plates I 61 are fixed and connected with the top wall of the inner shell 3 with bolts.

Figure 7:
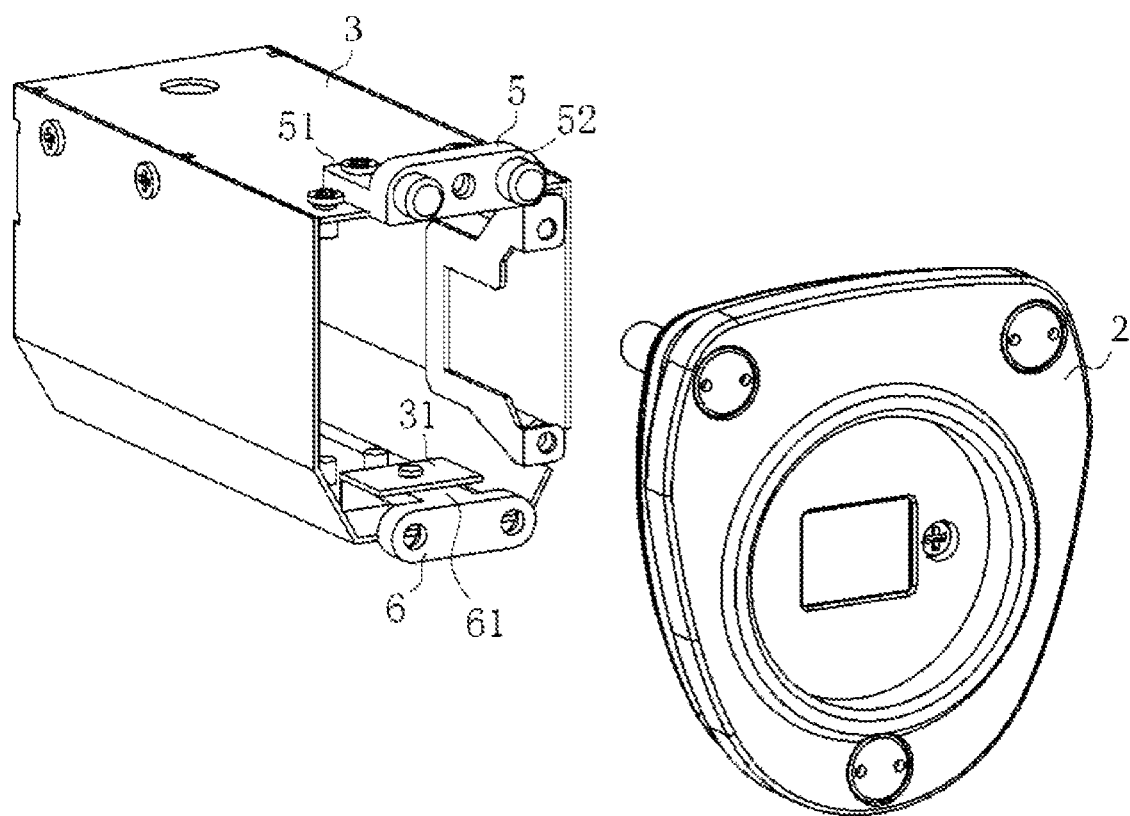
FIG. 7 is a structural view of the inner shell and the fixing plate in the embodiment.

As shown in FIGS. 6-7, fixing components also include a kidney-shaped strip fixing block II 7. A clamping groove II 244 is arranged in the sinking groove 24 for clamping the fixing block II 7; the fixing block II 7 can be fixed in the clamping groove II 244 with bolts. A fixing plate II 71 is provided on the side of the fixing block 7 away from the end cap 2; an L-shaped assembling plate 33 is provided on the inner bottom wall of the inner shell 3; the fixing plate II 71 can be fixed and connected with the assembling plate 33 with bolts. A rectangular frame-shaped fixing plate 31 is fixed at the open end of the inner shell 3; a fixing lug 311 is arranged on the fixing plate 31; the fixing lug 311 is fixed onto the inner shell 3 with a bolt. During assembling, the fixing plate II 71 is clamped between the fixing lug 311 and the assembling plate 33 at the bottom of the fixing plate 31, which are fixed with bolts; the fixing lug 311 at the top of the fixing plate 31 fits with the outer top wall of the inner shell 3 and is fixed with bolts.

Figure 8:
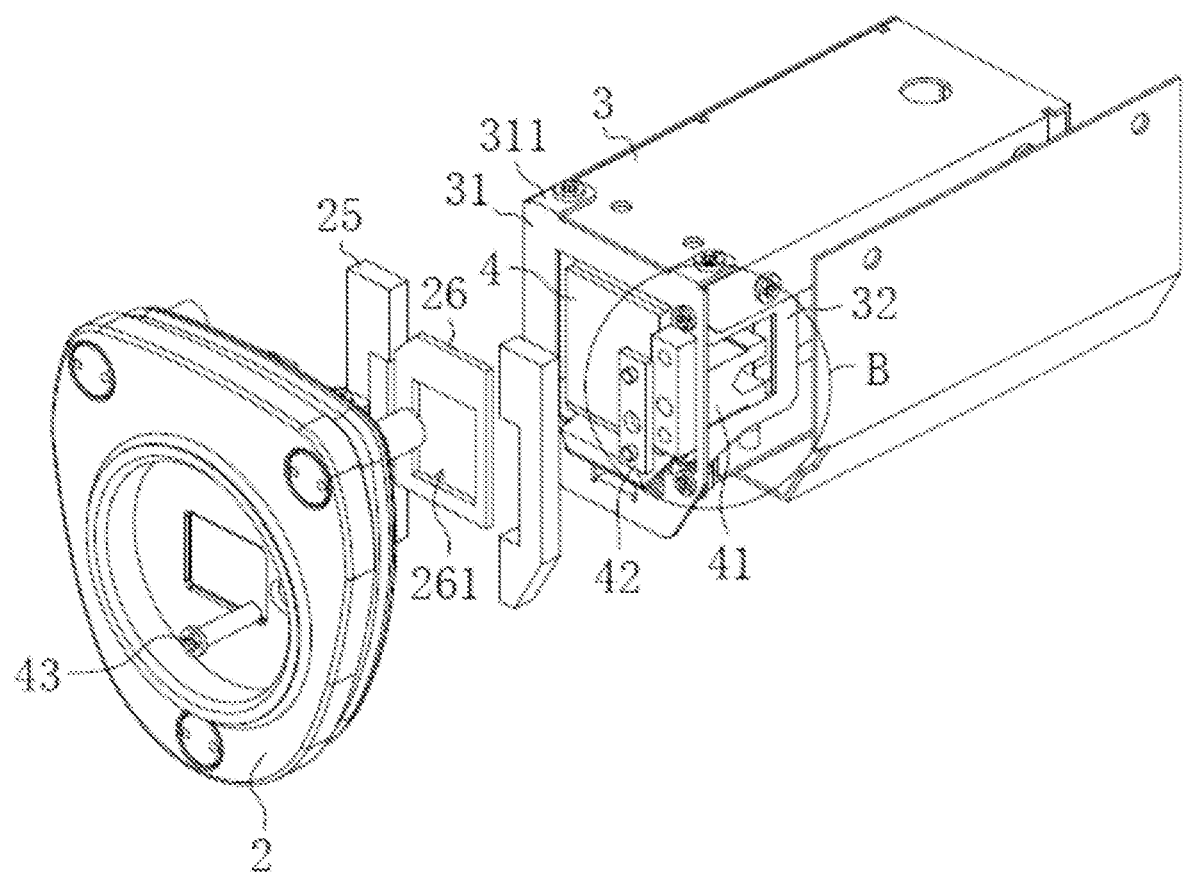
FIG. 8 is a structural view of the end cap, the inner shell, the sensor, the spacer block and the washer in the embodiment.

As shown in FIGS. 6 and 8, a lens group 5 is set at the light hole 241 on the end cap 2; imaging elements are provided inside the inner shell 3, including a 3MOS sensor 4; a spacer block 25 and a washer 26 are provided between the 3MOS sensor 4 and the lens group 5. A fixing groove 242 is arranged on the side of the light hole 241 of the end cap 2 toward the inner shell 3; the lens group 5 is fixed and assembled in the fixing groove 242. The lens group 5 comprises a dust blocking lens 51 and a light filtering lens 52; a clamping frame 53 is provided at the edge of the light filtering lens 52. The clamping frame 53 is of C-shape and has a clamping open 531 on the side toward the dust blocking lens 51 for clamping the light filtering lens 52. When assembling the lens group 5, a layer of UV sealant is applied on the bottom wall of the fixing groove 242; the dust blocking lens 51 is assembled into the fixing groove 242 and pressed tightly; UV sealant is cured with a UV light source; UV sealant is filled in the gaps between the dust blocking lens 51 and the side walls of the fixing groove 242, and then cured with a UV light source; the light filtering lens 52 is clamped into the clamping open 531 of the clamping frame 53; the light filtering lens 52 and the clamping frame 53 are assembled into the fixing groove 242; the light filtering lens 52 is made to tightly press the dust blocking lens 51; the clamping frame 53 is fixed and locked with a fixing screw; finally, UV sealant is filled in the gaps between the clamping frame 53, the light filtering lens 52 and the side walls of the fixing groove 242, and then cured with a UV light source; the lens group 5 is assembled. Common UV sealants available on the market can be used to assemble the lens group 5. The lens group 5 assembled with above method is firm and stable, and has excellent sealing and waterproof performances. External dusts and moisture are effectively blocked by the dust blocking lens 51, interference light waves are filtered by the light filtering lens 52, and the clear imaging of the camera handle is ensured.

As shown in FIGS. 6 and 8, the washer 26 is clamped between the light filtering lens 52 and the 3MOS sensor 4; a through-hole 261 is cut in the middle of the washer 26 for light to pass through. Direct contact of the 3MOS sensor 4 with the lens group 5 is avoided by setting the washer 26, and damages are prevented during assembling. Two spacer blocks 25 are clamped in the sinking groove 24 and provided on both sides of the washer 26. After assembling is finished, the spacer blocks 25 can form a support between the bottom wall of the sinking groove 24 and the fixing plate 31, and the fixing plate 31 is stably assembled. The spacer blocks 25 are of the same shape and can be randomly used during assembling.

Figure 9:
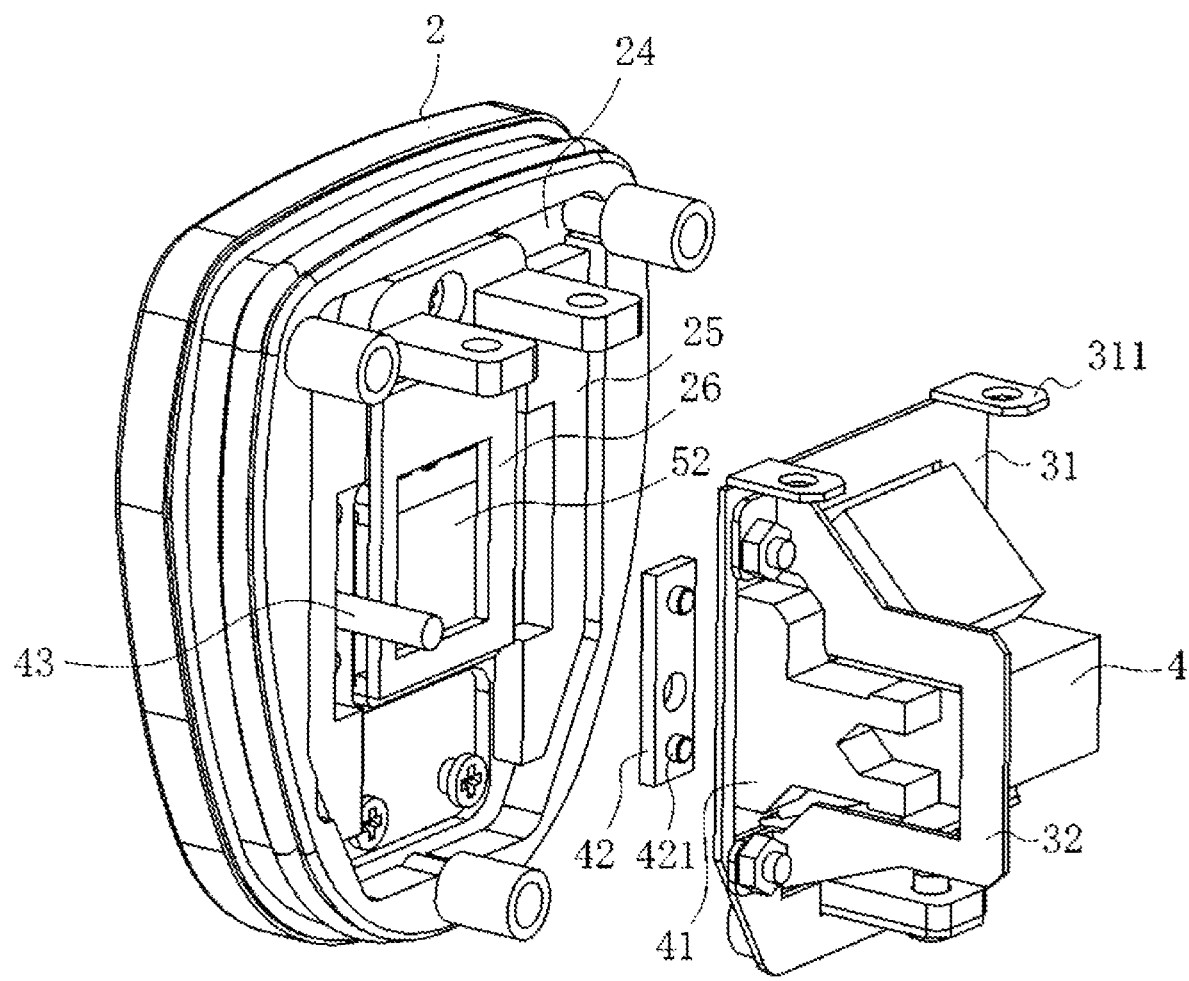
FIG. 9 is a structural view of the end cap, the fixing block, the positioning block and the sensor in the embodiment.
Figure 10:
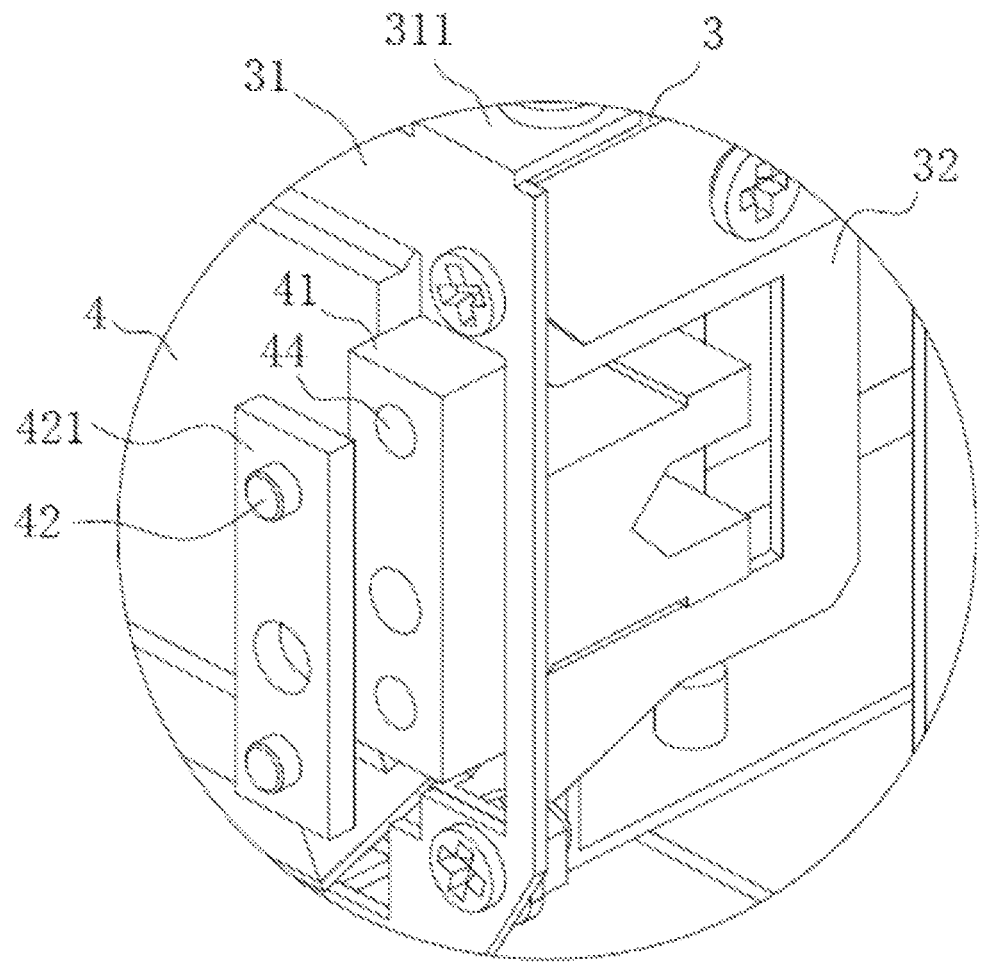
FIG. 10 is an enlarged view of Part B as shown in FIG. 8.

As shown in FIGS. 9-10, the 3MOS sensor 4 is provided inside the inner shell 3 (as shown in FIG. 8) and on the side of the fixing plate 31 away from the end cap 2. A fixing block 41 is fixedly set on one side of the 3MOS sensor 4; a positioning block 42 is fitted and provided on the side of the fixing block 41 toward the end cap 2. The fixing block 41 and the 3MOS sensor 4 are glued and fixed together with adhesive; the fixing block 41 and the positioning block 42 are fixed with a fixing bolt 43 on the side of the end cap 2 toward the inner shell 3. Several yield notches are cut on the fixing plate 31 and the spacer blocks 25 for assembling and fixing the 3MOS sensor 4 with the positioning block 42 and the fixing block 41. Several positioning lugs 421 are arranged on both sides of the positioning block 42; several positioning holes 44 are cut on the bottom wall of the sinking groove 24 and the end surface of the fixing block 41 for clamping the positioning lugs 421. A U-shaped metal radiating plate 32 is provided on the side of the fixing plate 31 away from the end cap 2; the radiating plate 32 is set around the fixing block 41 and between the 3MOS sensor 4 and the side wall of the inner shell 3 (as shown in FIG. 8). A threaded rod is provided on the fixing plate 31; the fixed end of the radiating plate 32 is set around the threaded rod; the radiating plate 32 is firmly fixed with the nut provided around the threaded rod.

Figure 11:
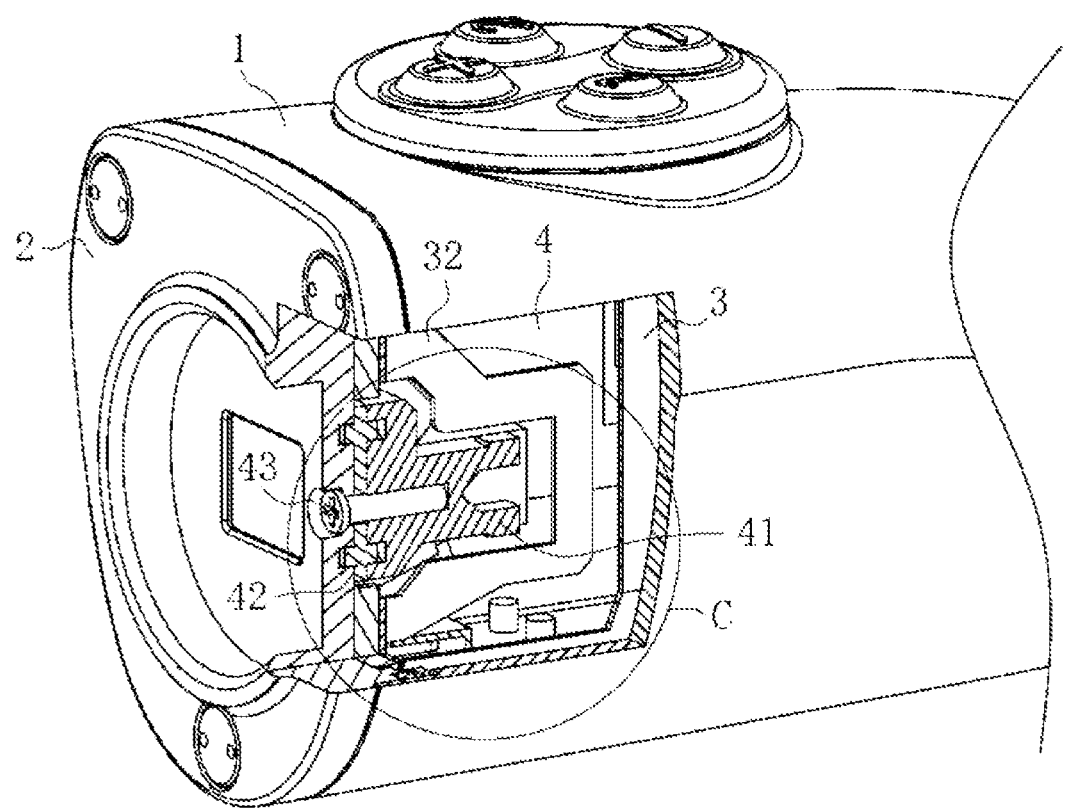
FIG. 11 is the sectional view II of the camera handle in the embodiment.
Figure 12:
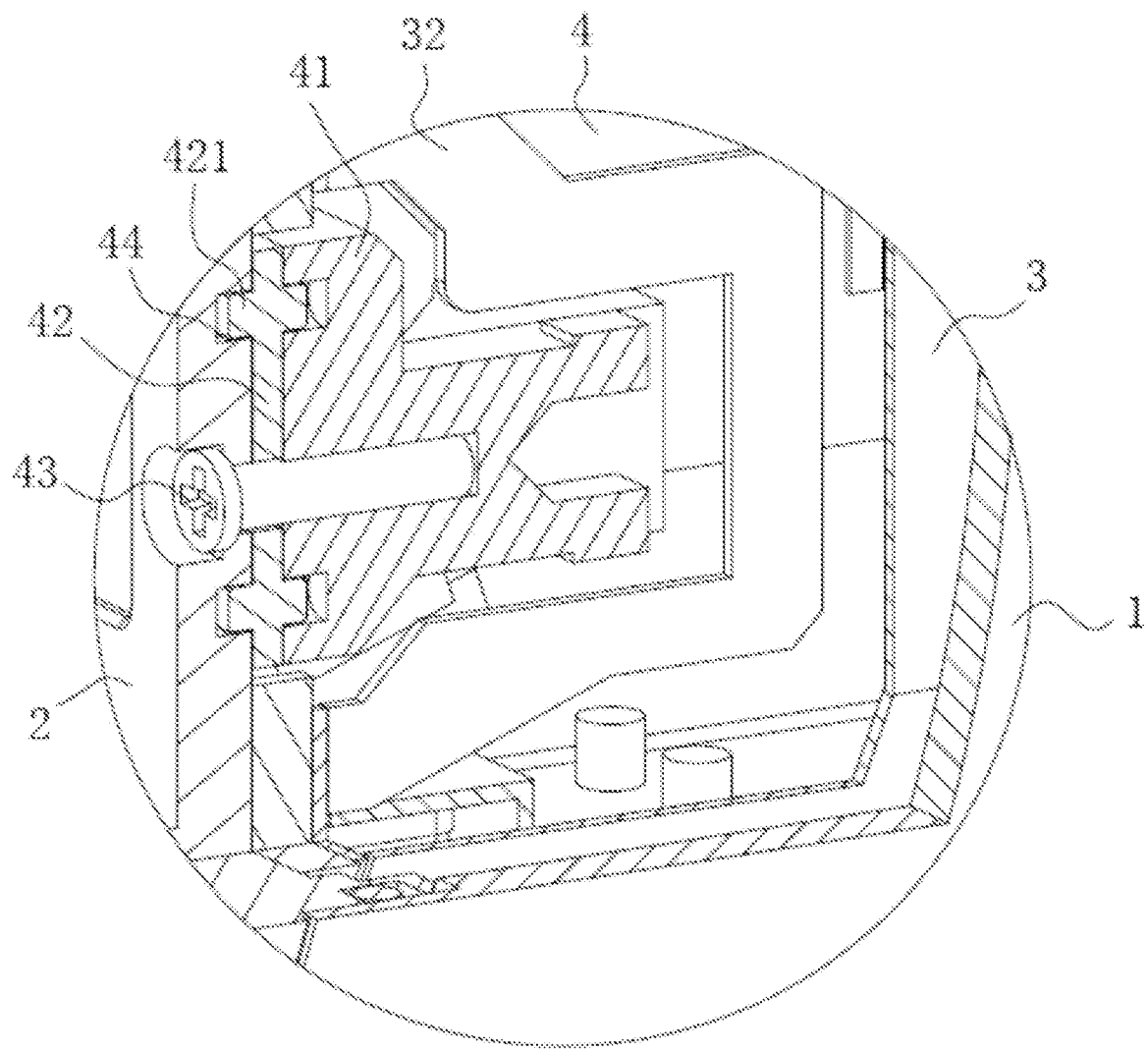
FIG. 12 is an enlarged view of Part C as shown in FIG. 11.

As shown in FIGS. 11~12, the fixing bolt 43 is inserted into the end cap 2; the fixing bolt 43 passes through the end cap 2 from the front of the end cap 2, then through the positioning block 42 and the fixing block 41; the positioning block 42 is clamped between the end cap 2 and the fixing block 41; the 3MOS sensor 4 is firmly fixed. Fixing the 3MOS sensor 4 with above method can minimize the number of screw holes. After the fixing bolt 43 is fastened, adhesive is applied at the head of the fixing bolt 43 for sealing, overall sealing and waterproof performances of the camera handle are improved. By fixing the 3MOS sensor 4 with above method, no additional supports from other fixing parts are required; the 3MOS sensor 4 will not be interfered easily by external factors; stable performances of splitting light and color reproduction of monochromatic lights are realized; stable imaging quality of the endoscope are ensured. Heat conduction rate is largely increased by setting the radiating plate 32; the heat generated in working process of the 3MOS sensor 4 is conducted away timely, and long time working stability of the 3MOS sensor 4 is realized; moreover, when assembling the 3MOS sensor 4, the radiating plate 32 plays a role of guiding and makes assembling more convenient. In order to further improve the shaping stability and anti-interference performance of the camera handle, an insulating layer can be formed on the inner side wall of the inner shell 3 by coating insulating paint and filling insulating foams inside the inner shell 3, in this way, negative impacts caused by external pulses and vibrations on the 3MOS sensor 4 can be minimized, and anti-interference performance of the camera handle can be improved.

Figure 13:
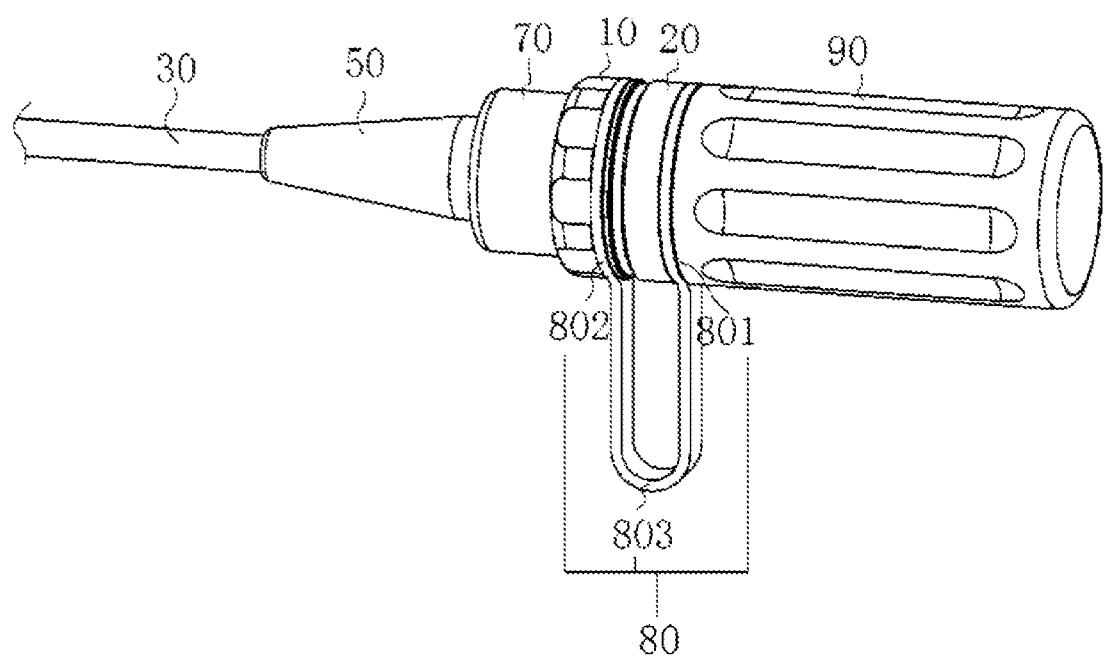
FIG. 13 is a structural view of the wired connector in the embodiment.
Figure 14:
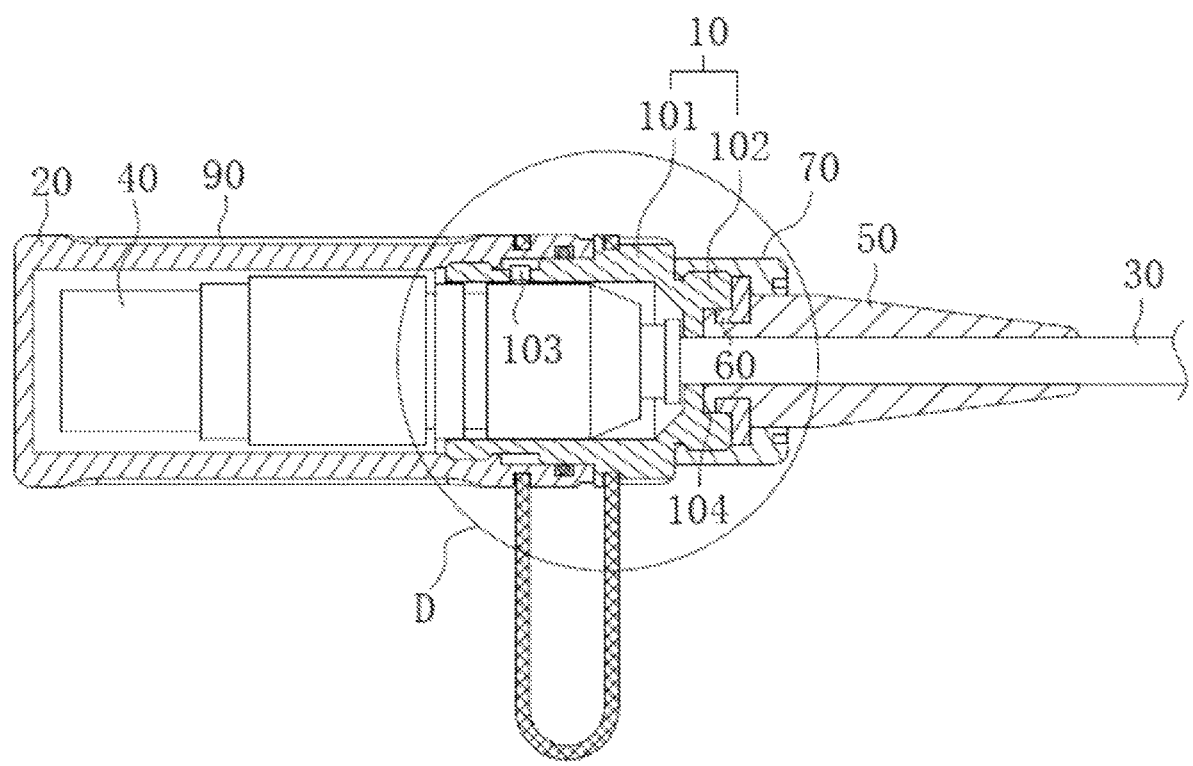
FIG. 14 is a sectional view of the wired connector in the embodiment.

A wired connector is connected with the tail of the camera handle, the waterproof sealing structure of the wired connector is described below. As shown in FIGS. 13~14, the wired connector comprises a connector 40, a sleeve 10, a wire 30 and a waterproof cover 20. The connector 40 is inserted into the sleeve 10, its tail is connected with the wire 30, and its head extends out of the sleeve 10 for connecting with corresponding device or instrument. The waterproof cover 20 is a circular tube, one of its ends is closed, and the other end is an open end set around the end of the sleeve 10.

As shown in FIGS. 13~14, a connecting part 80 is provided between the waterproof cover 20 and the sleeve 10 to prevent the waterproof cover 20 from losing. The connecting part 80 comprises a lantern ring I 801 set around the waterproof cover 20, a lantern ring II 802 set around the sleeve 10 and a flexible rope 803 connecting the lantern ring I 801 and the lantern ring II 802. In this embodiment, the lantern ring I 801, the lantern ring II 802 and the flexible rope 803 are made of flexible rubber and integrally molded. Ring grooves are arranged on the waterproof cover 20 and the sleeve 10 for assembling the lantern ring I 801 and the lantern ring II 802. Before using the wired connector 40, the waterproof cover 20 is removed; before and after using the wired connector 40, the waterproof cover 20 is set behind the end of the sleeve 10; the whole wired connector 40 is disinfected and will not be easily damaged by penetrated disinfectant.

Figure 15:
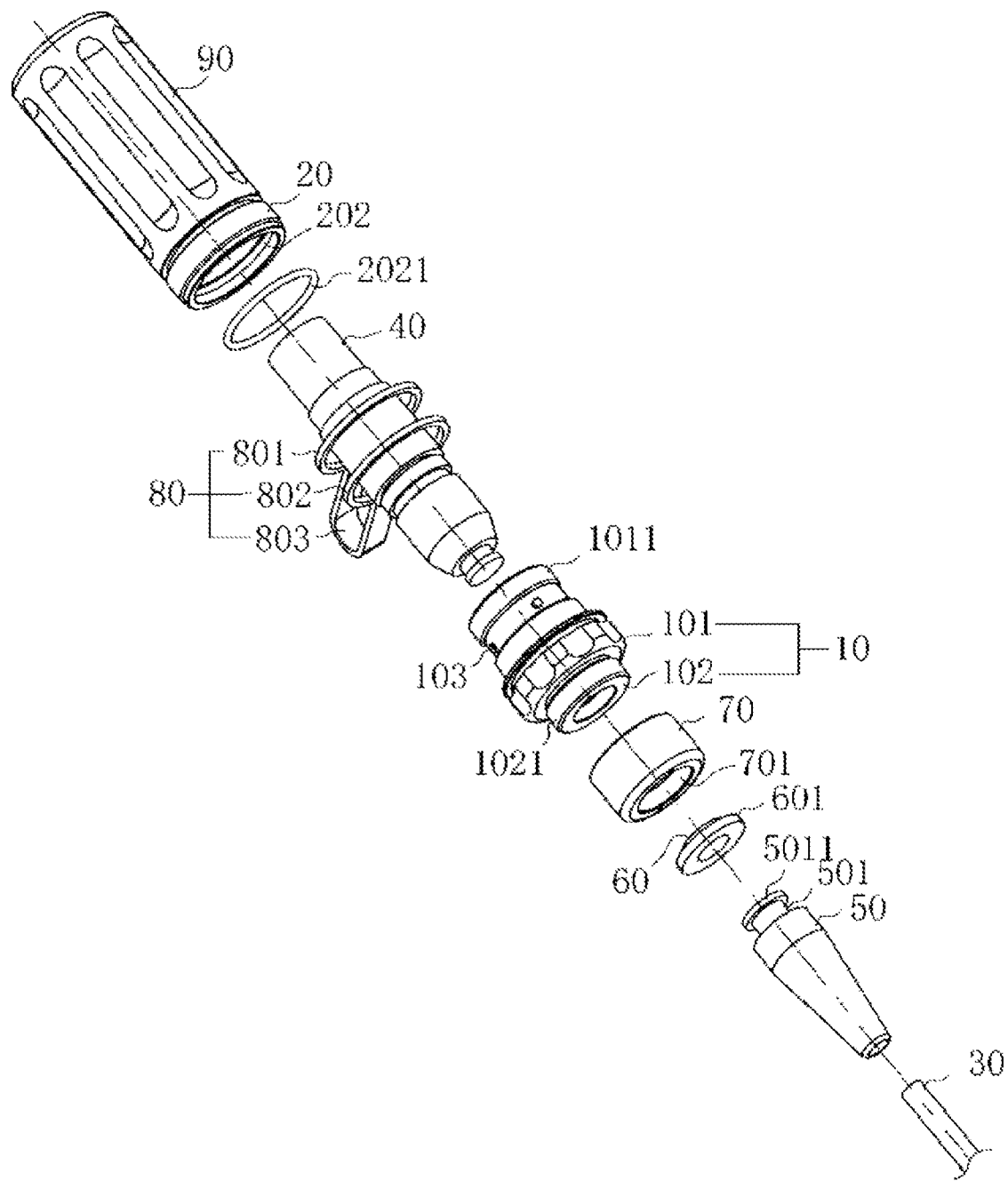
FIG. 15 is an exploded view of the wired connector in the embodiment.

As shown in FIGS. 14~15, for convenient holding the wired connector 40 when assembling or disassembling the waterproof cover 20, several strip grooves 90 are arranged on the outer circumferential side walls of the waterproof cover 20 and the sleeve 10 and along the axis direction of the waterproof cover 20. The roughness of the outer circumferential side walls of the waterproof cover 20 and the sleeve 10 is increased by arranging the grooves 90, and holding and pulling off the waterproof cover 20 become easier.

Figure 16:
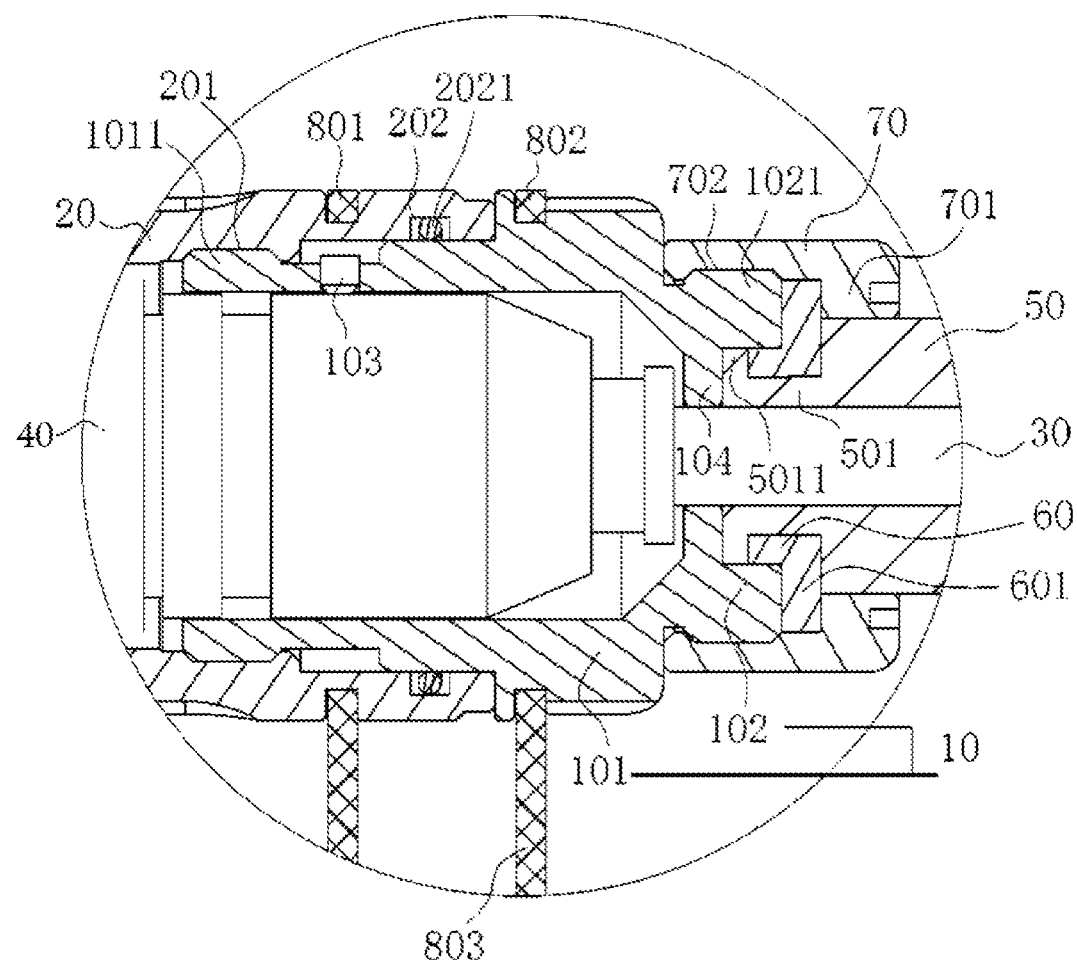
FIG. 16 is an enlarged view of Part D as shown in FIG. 14.

As shown in FIGS. 14 and 16, the sleeve 10 is divided into two sections arranged coaxially an assembling tube 101 and a fixing tube 102; a spacer plate 104 is provided at the connection of the assembling tube 101 and the fixing tube 102. The wired connector 40 is inserted into the assembling tube 101; the wire 30 passes through the space plate 104 and extends out of the fixing tube 102. A waterproof sealing assembly is provided at the end of the wire 30 extending out of the fixing tube 102 for firmly fixing the wire 30, and for preventing liquid and dusts from entering the inner cavity of the sleeve 10 through the gap between the wire 30 and the sleeve 10.

As shown in FIGS. 15~16, a first step section, a second step section and a third step section with diameters decreasing in turn are arranged on the outer circumferential side wall of the assembling tube 101 away from the fixing tube 102; a tongue and groove joint with a diameter as same as that of the second step section is arrange on the inner circumferential side wall of the waterproof cover 20 for setting the waterproof cover 20 around the end of the sleeve 10. A clamping ring edge I 1011 is arranged on the outer circumferential side wall of the third step section of the assembling tube 101; a ring groove I 201 is arranged on the inner circumferential side wall of the waterproof cover 20 for clamping the clamping ring edge I 1011. When assembling the waterproof cover 20, with clamping and cooperation between the clamping ring edge I 1011 and the ring groove I 201, the waterproof cover 20 is firmly assembled and will not get loose and fall easily.

As shown in FIGS. 15~16, in order to further enhance the tight assembling between the waterproof cover 20 and the assembling tube 101, and to improve sealing and waterproof performances, an assembling ring groove 202 is arranged at the tongue and groove joint in the inner cavity of the waterproof cover 20; an elastic sealing ring 2021 is provided in the assembling ring groove 202. After the waterproof cover 20 is sleeved onto the assembling tube 101, the elastic sealing ring 2021 fits with the outer circumferential side wall of the second step section of the assembling tube 101; the waterproof cover 20 and the sleeve 10 cooperate tightly; sealing and waterproof performances are greatly improved.

As shown in FIGS. 15~16, two positioning parts 103 are provided on the wall of the assembling tube 101 for fixing the wired connector 40 which is inserted into the assembling tube 101, and for preventing the wired connector 40 from getting loose; the connection between the wire 30 and the wired connector 40 will not crack/get loose easily. In this embodiment, two positioning parts 103 are provided along the wall of the assembling tube 101, and their ends tightly push against the jack screws of the wired connector 40. The angle between the axial lines of the two jack screws is 45°.

As shown in FIGS. 15~16, the waterproof sealing assembly comprises a sealing tube 50, a fixing ring 60 and a locking sleeve 70. The sealing tube 50 is made of flexible rubber and set around the wire 30. An insertion tube 501 with an outer diameter smaller than the inner diameter of the fixing tube 102 is provided at the end of the sealing tube 50 toward the sleeve 10; a limit ring edge I 5011 is arranged on the outer circumferential side wall at the end of the insertion tube 501. The limit ring edge I 5011 has an outer diameter as same as the inner diameter of the assembling tube 101, its end surface fits with the spacer plate 104, and its outer circumferential side wall fits with the inner circumferential side wall of the assembling tube 101. A fixing ring 60 is coaxially arranged around the insertion tube 501; the radial thickness of the fixing ring 60 equals to the difference between the inner diameter of the fixing tube 102 and the outer diameter of the insertion tube 501. A limit ring edge II 601 is arranged on the outer circumferential side wall of the end of the fixing ring 60 away from the spacer plate 104; the outer diameters of the limit ring edge II 601 and the fixing tube 102 are the same. After assembling is finished, with the existence of the fixing ring 60, the insertion tube 501 and the limit ring edge I 5011 tightly fit with the spacer plate 104 and the inner circumferential side wall of the fixing tube 102; excellent sealing and waterproof performances are realized.

As shown in FIGS. 15~16, the locking sleeve 70 is used to fix the sealing tube 50 and the fixing ring 60; the inner diameter of the locking sleeve 70 and the outer diameter of the fixing tube 102 are the same; a limit ring edge III 701 is arranged on the inner circumferential side wall of the end of the locking sleeve 70 away from the sleeve 10; the inner diameter of the limit ring edge III 701 and the outer diameter of the sealing tube 50 are the same. After assembling is finished, the limit ring edge III 701 tightly pushes the limit ring edge II 601 against the end of the fixing tube 102; the sealing tube 50 will not get loose easily.

As shown in FIGS. 15~16, a clamping ring edge II 1021 is arranged on the outer circumferential side wall of the fixing tube 102; a ring groove II 702 is arranged on the inner circumferential side wall of the locking sleeve 70 for clamping the clamping ring edge II 1021. With clamping and cooperation between the clamping ring edge II 1021 and the ring groove II 702, the locking sleeve 70 is firmly assembled onto the fixing tube 102 of the sleeve 10 and will not fall easily.

As shown in FIG. 15, in order to adapt to curving or bending of the wire 30, the outer diameter of the section of the sealing tube 50, which extends out of the fixing tube 102 and is away from the sleeve 10, gradually decreases to make the section of the sealing tube 50 away from the sleeve 10 more flexible, to better adapt to the curving/bending of the wire 30, to prevent the wire 30 from cracking under inflexible bending or disconnecting from the wired connector 40, and to improve the durability and safety of the wired connector 40.

Working Principle

The endoscope needs to be disinfected with disinfectant before use, and it may contact with body fluids during use; therefore, the endoscope is required to have excellent sealing and waterproof performances, and its imaging quality shall not be affected. In order to satisfy above requirements, the outer shell 1, the inner shell 3 and the end cap 2 are fixed together onto the camera handle with the fixing block 41, the positioning block 42 and the fixing bolt 43; many sealing rings are provided to seal the gaps existing after the spacer parts are assembled; disinfectant and body fluids can't easily penetrate into the camera handle and damage the electronic components inside the camera handle. For the wired connector 40, the waterproof sealing assembly is provided; the waterproof cover 20 is provided on the head of the wired connector 40; the elastic sealing ring 2021 between the waterproof cover 20 and the wired connector 40 isolates the internal space of the waterproof cover 20 from external space; in this way, disinfection of the wired connector 40 becomes easier, and using will not be affected because the wired connector 40 is wet by disinfectant.

Above technical schemes only represent the preferred technical schemes of the present invention; all the changes in above technical schemes made by those skilled in the art reflect the principles and under the protection scope of the present invention.

What is claimed is:

1. An endoscope comprising a camera handle used to fix a camera lens, and a wired connector which is connected to a power supply for providing power to the endoscope, wherein, the camera handle comprises an outer shell, an end cap inserted and assembled to one end of the outer shell, an inner shell provided inside the outer shell, and a sensing element provided inside the inner shell, a lens group is provided between the sensing element and the end cap, the inner shell is fixedly connected to the outer shell by assembling components, the outer shell is fixedly connected to the inner shell, and a light hole is arranged in a middle position of the end cap and corresponds to the position of the sensing element, the wired connector comprises a wire, a connector connected to the wire, and a sleeve wrapping the connector, wherein one end of the connector extends beyond the sleeve, a waterproof cover is provided around the one end of the connector, the waterproof cover is cylindrical, one end of the waterproof cover is open and the other end of the waterproof cover is closed, and a waterproof sealing assembly is provided at one end of the sleeve for fixing the wire wherein the one end of the sleeve is away from the waterproof cover, and the sleeve comprises an assembling tube and a fixing tube, wherein the assembling tube and the fixing tube are coaxially arranged, and an outer diameter of the fixing tube is smaller than an outer diameter of the assembling tube, a spacer plate is provided at a connection position of the assembling tube and the fixing tube, the connector is inserted into the assembling tube, an assembling ring groove is arranged on an inner circumferential side wall of the waterproof cover, and an elastic sealing ring is provided in the assembling ring groove for fitting with an outer circumferential side wall of the sleeve.

2. The endoscope of claim 1, wherein, an insertion section is provided at an edge of the end cap and is inserted into and connected to the outer shell, a fixing groove is arranged on an outer ring surface of the insertion section, and a sealing ring I is provided in the fixing groove, and the fixing components comprise a plurality of anchor bolts inserted into the end cap, and a plurality of insertion tubes corresponding to the anchor bolts are provided on an inner side wall of the outer shell.

3. The endoscope of claim 2, wherein,
each of the anchor bolts comprises a bolt head and a bolt shank,
a ring groove is arranged on an outer ring surface of the bolt shank,
a sealing rings II is provided in the ring grooves, and
a sleeve is sleeved onto the outer ring surface of the bolt shank, and the sleeve and the bolt shank transiently fit with the insertion tubes.

4. The endoscope of claim 1, wherein,
a washer is provided between the lens group and the sensing element,
a fixing groove is arranged at the position of the light hole of the end cap for assembling the lens group,
the lens group comprises a dust blocking lens and a light filtering lens, wherein the light filtering lens is provided between the dust blocking lens and the washer,
a clamping frame is provided at an edge of the light filtering lens, wherein the clamping frame is of C-shape and has a clamping open toward the dust blocking lens for clamping the light filtering lens, and the clamping frame is fixedly connected to the end cap.

5. The endoscope of claim 4, wherein the lens group is fixed and assembled to the light hole of the end cap by following steps:
   S1. apply a layer of UV sealant on a bottom wall of the fixing groove, assemble the dust blocking lens to the fixing groove, and cure the UV sealant with a UV light source;
   S2. fill the UV sealant into gaps between side walls of the dust blocking lens and the fixing groove, and cure the UV sealant with the UV light source;
   S3. clamp the light filtering lens to the clamping open of the clamping frame, assemble the light filtering lens and the clamping frame in the fixing groove, press tightly the light filtering lens to the dust blocking lens, and fix the clamping frame; and
   S4. fill the UV sealant into the gaps among side walls of the clamping frame, the light filtering lens and the fixing groove, cure the UV sealant with the UV light source, and assemble the lens group.

6. The endoscope of claim 1, wherein,
the waterproof sealing assembly comprises a sealing tube, a fixing ring and a removable locking sleeve, wherein the removable locking sleeve is connected to the fixing tube,
the sealing tube is provided around the wire,
an insertion tube is provided at one end of the sealing tube and inserted into the fixing tube,
a limit ring edge I is arranged on an outer circumferential side wall of one end of the insertion tube, wherein the one end of the insertion tube is fitted with the spacer plate,
the fixing ring is provided around the insertion tube, one end of the fixing ring is inserted into the fixing tube, and an outer circumferential side wall of the other end of the fixing ring is arranged with a limit ring edge II fitted with an end surface of the fixing tube, and
a limit ring edge III is arranged on an inner circumferential side wall of one end of the locking sleeve, wherein the one end of the locking sleeve is away from the spacer plate, and an inner diameter of the limit ring edge III is smaller than an outer diameter of the limit ring edge II.

7. The endoscope of claim 1, wherein,
a positioning part is provided on a wall of the sleeve and is used to fix the connector, and a connecting part is provided between the sleeve and the waterproof cover.

8. The endoscope of claim 7 wherein,
the connecting part comprises a lantern ring I, a lantern ring II, and a flexible rope, wherein the lantern ring I is set around the waterproof cover, the lantern ring II is set around the sleeve, and the flexible rope connects the lantern ring I to the lantern ring II.

* * * * *